US011383011B2

(12) United States Patent
Elbadry

(10) Patent No.: US 11,383,011 B2
(45) Date of Patent: Jul. 12, 2022

(54) SYSTEMS AND METHODS FOR GASTRIC DIALYSIS

(71) Applicant: GastroKlenz Inc., San Francisco, CA (US)

(72) Inventor: Aly R. A. A. Elbadry, San Francisco, CA (US)

(73) Assignee: GASTROKLENZ INC., San Francisco, CA (US)

(*) Notice: Subject to any disclaimer, the term of this patent is extended or adjusted under 35 U.S.C. 154(b) by 138 days.

(21) Appl. No.: 16/200,261

(22) Filed: Nov. 26, 2018

(65) Prior Publication Data

US 2019/0091393 A1    Mar. 28, 2019

Related U.S. Application Data

(63) Continuation of application No. PCT/US2017/034796, filed on May 26, 2017.
(Continued)

(51) Int. Cl.
*A61M 1/16* (2006.01)
*B01D 61/24* (2006.01)
(Continued)

(52) U.S. Cl.
CPC ............ *A61M 1/1621* (2014.02); *A61M 1/14* (2013.01); *A61M 1/1654* (2013.01); *A61M 1/28* (2013.01);
(Continued)

(58) Field of Classification Search
CPC .... A61M 1/1621; A61M 1/28; A61M 1/1654; A61M 1/287; A61M 1/14;
(Continued)

(56) References Cited

U.S. PATENT DOCUMENTS 6,979,351 B2    12/2005    Forsell et al.
2006/0058731 A1    3/2006    Burnett et al.
(Continued)

FOREIGN PATENT DOCUMENTS

CN    104271175 A    1/2015
WO    WO 2013/051680 A1    4/2013
WO    WO-2013122580 A1 *    8/2013    .......... A61M 1/1676

OTHER PUBLICATIONS

International Search Report and Written Opinion dated Oct. 13, 2017 in International Application No. PCT/US2017/034796, 11 pages.
(Continued)

*Primary Examiner* — Nathan R Price
*Assistant Examiner* — Tasnim Mehjabin Ahmed
(74) *Attorney, Agent, or Firm* — Cooley LLP

(57) ABSTRACT

Devices, systems, and methods herein relate to performing dialysis to manage a chronic condition such as end-stage renal disease. These systems and methods may allow a patient to orally ingest a potable dialysate and excrete the dialysate via the urinary tract. In some variations, a method may include delivering a dialysate via the esophagus of a patient and draining the dialysate into a bladder of the patient. Delivering the dialysate may further comprise delivering the dialysate through the nasopharynx or oropharynx. Delivering the dialysate through the oropharynx may comprise the patient drinking the dialysate.

13 Claims, 13 Drawing Sheets

Related U.S. Application Data

(60) Provisional application No. 62/342,520, filed on May 27, 2016.

(51) Int. Cl.
 B01D 61/28 (2006.01)
 B01D 63/08 (2006.01)
 A61M 1/28 (2006.01)
 A61M 1/14 (2006.01)
 A61F 2/48 (2006.01)

(52) U.S. Cl.
 CPC ........... A61M 1/287 (2013.01); B01D 61/243 (2013.01); B01D 61/28 (2013.01); B01D 63/087 (2013.01); *A61F 2/482* (2021.08); *A61M 2210/105* (2013.01); *A61M 2210/1017* (2013.01); *A61M 2210/1053* (2013.01); *A61M 2210/1085* (2013.01)

(58) Field of Classification Search
 CPC ...... A61M 2210/1017; A61F 2002/482; B01D 61/243; B01D 61/28
 See application file for complete search history.

(56) References Cited

U.S. PATENT DOCUMENTS

2012/0325330 A1* 12/2012 Prince ............... A61M 5/16881
 137/2
2014/0148754 A1 5/2014 Soykan et al.

OTHER PUBLICATIONS

GastroKlenz, GastroKlenz Demo., Dec. 1, 2016 (Dec. 1, 2016), XP054978046, Retrieved from the Internet <URL:https://www.youtube.com/playlist?list=PLY3-aJUCyz9y8MQLInPTzwgR8IBVNuys3> [retrieved on Jul. 12, 2019].

* cited by examiner

SYSTEMS AND METHODS FOR GASTRIC DIALYSIS

CROSS-REFERENCE TO RELATED APPLICATIONS

This application is a continuation application of International Application No. PCT/US2017/034796, filed May 26, 2017, and titled "SYSTEMS AND METHODS FOR GASTRIC DIALYSIS," which claims the benefit of U.S. Provisional Application No. 62/342,520, filed May 27, 2016, and titled "GASTRIC DIALYSIS," the contents of each of which are hereby incorporated by reference in their entireties.

FIELD

Devices, systems, and methods herein relate to performing dialysis using an orally ingestible dialysate that may be used in managing a chronic disease, including but not limited to end-stage renal disease (ESRD).

BACKGROUND

End-stage renal disease (ESRD) is a chronic disease in which a patient's kidneys fail to perform their function of filtering waste and excess fluid from the blood and delivering these waste products to the bladder for urination. ESRD is conventionally treated through one or more of a kidney transplant, hemodialysis, and peritoneal dialysis. A kidney transplant replaces a patient's poorly functioning kidneys with a healthy kidney from another person. However, the demand for suitable transplant kidneys far outweighs the available supply, and also requires transplant recipients to receive lifelong immunosuppressant medication to reduce the likelihood of patient rejection of the transplanted kidney. Hemodialysis utilizes a dialysis machine to filter a patient's blood, before returning the blood to the patient's body. A patient typically undergoes hemodialysis at a medical facility on a predetermined basis (e.g., 3-4 treatment sessions per week for 3-4 hours per session) to ensure the timely removal of metabolites. The frequency and length of the treatment sessions may interfere with a patient's lifestyle (e.g., ability to travel) and ability to maintain a desired schedule (e.g., full-time work, academics). Hemodialysis treatments may be costly for patients and/or insurers due to on-going personnel, facility, and energy costs. Peritoneal dialysis (PD) is performed by introducing and removing dialysate from a patient's peritoneal cavity using a catheter placed through a patient's body (e.g., abdomen). The dialysate absorbs waste and fluid from the blood using the peritoneum as a filter. Peritoneal dialysis techniques include continuous ambulatory peritoneal dialysis (CAPD) and continuous cycler-assisted PD (CCPD). PD suffers from higher rates of infection due to the use of a catheter that protrudes from the patient's body and may not be suitable for certain patient populations (e.g., seniors, patients with limited mobility or morbid obesity). In another example, some diabetic patients may not be suitable for PD due to the sugar content of a dextrose-based dialysate. As such, it may be desirable to provide a patient with additional systems, devices, and methods for performing dialysis.

SUMMARY

Described here are systems and methods for performing dialysis using an orally ingestible dialysate that may be urinated by a patient and used to manage a chronic condition such as ESRD. Intake and excretion of the dialysate utilizes existing pathways and may be used to permit mobile dialysis treatment that may be self-administered by the patient. A dialysate compartment may be formed to hold the dialysate and a pathway may be formed between the dialysate compartment and a urinary tract. The patient may selectively permit ingested matter to flow into a stomach compartment for digestion and a dialysate compartment for dialysis. A set of valves implanted in the patient may control the flow of the dialysate through the body and may be monitored electronically.

Generally, the methods described herein of performing dialysis for a patient may include delivering a dialysate via the esophagus of a patient and draining the dialysate into a bladder of the patient. Delivering the dialysate may further comprise delivering the dialysate through the nasopharynx or oropharynx. Delivering the dialysate through the oropharynx may comprise the patient drinking the dialysate.

In some variations, a first valve disposed in a gastroesophageal junction or gastric cavity of the patient may be transition between a first configuration and a second configuration. The first configuration may be configured to form a first path between the esophagus and a stomach compartment. The second configuration may be configured to form a second path between the esophagus and a dialysate compartment. A dialysate ingested orally may be configured to flow through the second path and into the dialysate compartment. The dialysate may be removed from the dialysate compartment after a predetermined amount of time.

In some variations, a method of performing dialysis may include transitioning a second valve between a closed position and an open position where the second valve couples the dialysate compartment and a urinary tract. The second valve may be configured to permit the dialysate in the dialysate compartment to flow into the urinary tract and be urinated.

In some variations, removing the dialysate may comprise withdrawing the dialysate through a catheter or conduit disposed through an abdominal wall of the patient and into the dialysate compartment. In some variations, the first valve may be transitioned between the second configuration and a third configuration. The third configuration may be configured to advance ingested matter disposed in the first valve into the stomach compartment. In some variations, the first valve may comprise one or more discs. An actuator may be coupled to the one or more discs, and a filter may be disposed within the second path and configured to inhibit a non-dialysate from passing into the dialysate compartment. In some of these variations, the first valve may be transitioned between the first configuration and the second configuration comprises rotating one or more of the discs using the actuator. In some variations, the first valve may be a bi-directional valve, and the second valve may be a unidirectional valve. In some variations, UV light may be emitted within the first valve using a UV light source of the first valve.

Methods of forming a dialysis system are also described and may include separating the stomach into the stomach compartment and the dialysate compartment. In some of these variations, a selective vagotomy, nerve block or denervation procedure may be performed to the nerves innervating the dialysate compartment. In some variations, a dialysate channel may be formed to fluidly couple the dialysate compartment to one or more of the bladder and ureter of the urinary tract. In some of these variations, the second valve may be disposed between the dialysate compartment and the dialysate channel.

Also described here are devices. In some variations, a device is provided, and may include a transceiver configured to communicate with a gastroesophageal junction valve disposed in a patient. An input device may be configured to receive a control signal to control dialysate fluid flow through the gastroesophageal junction valve. An output device may be configured to output data to the patient. A controller may be coupled to the transceiver, the input device, and the output device. The controller may comprise a processor and a memory. The controller may be configured to control the gastroesophageal junction valve such that the dialysate advances into a dialysate compartment and a non-dialysate advances into a stomach compartment.

In some variations, the transceiver may be configured to communicate with a urinary tract valve each disposed in a patient, the input device may be configured to receive the control signal from the urinary tract valve, and the controller may be configured to open the urinary tract valve such that the dialysate in the dialysate compartment is permitted to flow into a urinary tract for urination.

In some of these variations, the controller may be configured to output a first prompt to ingest the dialysate using a predetermined schedule using a computing device comprising a processor and memory, and output a second prompt to transition the second valve to the open position using the predetermined schedule. In some of these variations, the controller may be configured to notify a set of predetermined contacts of a status of the first and second valve.

In some variations, the controller may be configured to advance ingested matter held within the gastroesophageal junction valve into the stomach compartment. In some variations, the controller may be configured to control the gastroesophageal valve using proximity data of the patient and dialysate generated by a proximity sensing device.

In some variations, a valve is provided, and may include a housing comprising an input port, a first output port, a second output port, a transceiver, an actuator, and a controller. The transceiver may be configured to communicate with a computing device. The actuator may be coupled to the one or more discs. The controller may be coupled to the transceiver and the actuator. The controller may comprises a processor and a memory. The controller may be configured to control a position of the one or more discs such that the dialysate advances into a dialysate compartment and a non-dialysate advances into a stomach compartment. In some variations, the valve may include a filter disposed in the housing between the input port and the second output port.

Also described herein are methods of treatment including implanting a first valve between a first gastrointestinal region, a second gastrointestinal region, and a third gastrointestinal region. In some variations, a conduit may be implanted between the third gastrointestinal region and a peritoneal cavity of the patient. In some variations, a peritoneal cavity may be inserted into the patient. In some variations, a second valve may be implanted between the peritoneal cavity and a bladder cavity of the patient. In some of these variations, the first gastrointestinal region may be an esophagus. In some of these variations, the second and third gastrointestinal regions may be gastric subcavities separated by sutures or staples or a surgically formed gastric wall.

Additional methods may include placing a guidewire system along an anatomical path that includes at least two anatomical path segments from a group of path segments between an esophagus and a gastric cavity, the gastric cavity and a peritoneal cavity, the peritoneal cavity and a bladder cavity, and the bladder cavity and a urethra. In some variations, the guidewire system placed along the anatomical path may include at least three of the anatomical path segments. In some variations, the guidewire system may be placed along the anatomical path including all of the anatomical path segments.

In some of these variations, placing the guidewire system may comprise placing a single guidewire along the anatomical segments. In some variations, the guidewire system may comprise at least a first and a second guidewire. Placing the guidewire system may comprise inserting the first guidewire into the esophagus and inserting the second guidewire into the urethra.

BRIEF DESCRIPTION OF THE DRAWINGS

FIG. 6A is a cut-away perspective view, and FIGS. 6B-6D are cross-sectional schematic views.

DETAILED DESCRIPTION

Figure 1A:
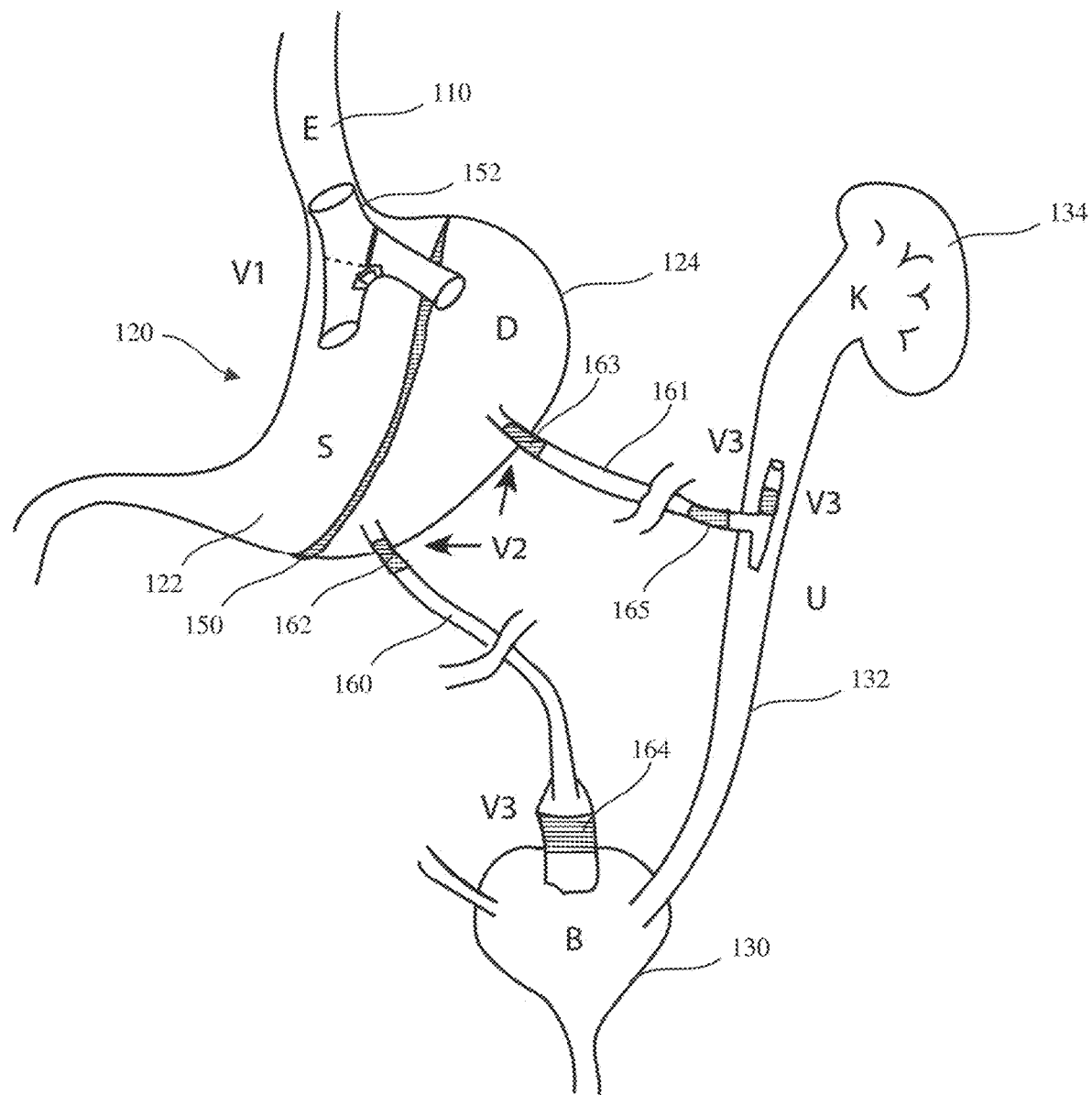
FIGS. 1A-1B are illustrative views of exemplary variations of disease management systems in patient anatomy.

Described here are systems, devices, and methods for performing dialysis through oral ingestion and micturition using a dialysate and a set of valves implanted in a patient. Generally, the systems and methods described herein may include a potable dialysate that may be orally ingested through the mouth. The dialysate may travel through a patient's esophagus and into a designated dialysate compartment of the body configured to hold the dialysate for a predetermined amount of time, thereby permitting removal of waste products of the patient through membrane filtering. After a predetermined amount of time, the dialysate held in the dialysate compartment may be permitted to flow into the urinary tract for a patient to urinate out of the body. Control of dialysate flow through the dialysate compartment and urinary tract may be regulated using a set of valves such as a gastroesophageal valve and one or more urinary tract valves.

In some variations, a gastroesophageal valve may be used to direct matter traveling through an esophagus (e.g., dialysate and non-dialysate matter) into a predetermined body cavity (e.g., stomach compartment, dialysate compartment). The dialysate compartment may be formed by, for example, gastric division (e.g., sleeve gastroplasty) where a portion of the stomach is used to form a body cavity (e.g., dialysate compartment) configured to hold the dialysate. In some variations, the body cavity may be one or more of the peritoneal cavity, a detached gastric sleeve compartment, and a surgically formed compartment (e.g., using portions of the omental and/or peritoneal membrane). In some variations, the gastroesophageal valve may include one or more safety mechanisms configured to advance non-dialysate matter (e.g., food) out of a dialysate pathway and into the stomach compartment.

In order to provide a pathway for waste product excretion, a laparoscopic procedure may be performed to surgically form a dialysate channel from the dialysate compartment to the urinary tract. One or more urinary tract valves (e.g., bladder valve, urethra valve) may be used to control unidirectional flow of the dialysate from the dialysate compartment to the urinary tract (e.g., bladder, urethra).

In some variations, a device such as an external computing device (e.g., mobile device, smartphone, tablet, phablet, laptop, PDA, desktop PC) may be configured to control operation of the set of valves. The computing device may be further configured to aid the patient in performing the dialysis by operating the valves using a predetermined schedule, outputting patient prompts, and transmitting patient data (e.g., patient and valve status, compliance data) to one or more of a remote database and a set of predetermined contacts (e.g., health care professional, family members) based on predetermined criteria.

I. Methods

Described here are methods for performing dialysis of a patient using the systems and devices described herein. Generally, the methods described here include directing ingested matter (e.g., food, dialysate) into one of a stomach compartment and a surgically-constructed dialysate compartment using a selectable valve disposed in a gastroesophageal junction of the patient. Dialysate within the dialysate compartment may be configured to flow into a urinary tract through one or more urinary tract valves disposed in one or more surgically-constructed dialysate channels connecting the dialysate compartment to the urinary tract. The methods described here may permit a patient to easily perform dialysis through oral ingestion and urination of a dialysate. This may have one or more benefits, such as permitting dialysis to be performed at a desired location (e.g., not limited to a medical facility such as a dialysis center). Accordingly, the cost of dialysis treatment may be reduced through more efficient use of medical resources (e.g., facilities and personnel). The dialysis process may be monitored using sensors to ensure patient safety and compliance. The methods described herein may be suitable for a larger proportion of the patient population than conventional dialysis methods such as peritoneal dialysis. For example, the dialysate used herein may be a non-dextrose-based solution that may be ingestible by diabetic patients.

Generally, the methods described here include forming a dialysate compartment and a pathway from a patient esophagus to the dialysate compartment. A dialysate removal pathway may be formed to permit removal of dialysate from the body. A dialysate may be orally ingested by the patient for dialysis in the dialysate compartment. At a predetermined time, the dialysate may be removed from the body, such as through urination. FIG. 2 is a flowchart that generally describes a method of performing dialysis and includes an implantation process (200) performed by a surgeon and a dialysis process (250) performed by a patient. The implantation process (200) may begin by forming a dialysate compartment and/or flow path from the esophagus to the dialysate compartment (202). As described in more detail with respect to FIGS. 1A-1B, the dialysate compartment may be surgically formed from one or more of the stomach, omentum, and peritoneum, or may be the peritoneal cavity. For example, one or more portions of the omentum may be joined to one or more portions of the peritoneum laparoscopically. The joined portions may be sealed by, for example, sutures and/or energy-based devices such as ligating devices. In variations where the dialysate compartment is formed from the stomach, a stomach compartment may be formed using laparoscopic techniques using devices such as a scope, graspers, and stapler. A bougie may be utilized to size one or more of the stomach compartment and dialysate compartment. For example, a 32-36 French sized bougie may create an about 0.5 inch diameter sleeve compartment. The stapler may seal the compartment.

A gastroesophageal valve may be surgically implanted in a gastroesophageal junction or gastric cavity of a patient to provide a selectable flow path from the esophagus to one of a stomach compartment and a dialysate compartment. The valve may be implanted using laparoscopic and/or endoscopic techniques. For example, the valve may comprise one or more anchoring mechanisms such as surgical sutures, staples, and hooks for securing into tissue.

A dialysate removal pathway may be formed to permit the dialysate to be removed from the body (204). For example, a dialysate channel may be formed to couple the dialysate compartment to the urinary tract (e.g., bladder, ureter). The dialysate channel may be formed using laparoscopic techniques and may utilize artificial grafts. One or more valves may be disposed between the dialysate compartment and urinary tract to control the flow of dialysate into the urinary tract. In other variations, a catheter or conduit may be placed through a patient's abdominal wall and into the dialysate compartment to permit removal of dialysate.

Figure 1B:
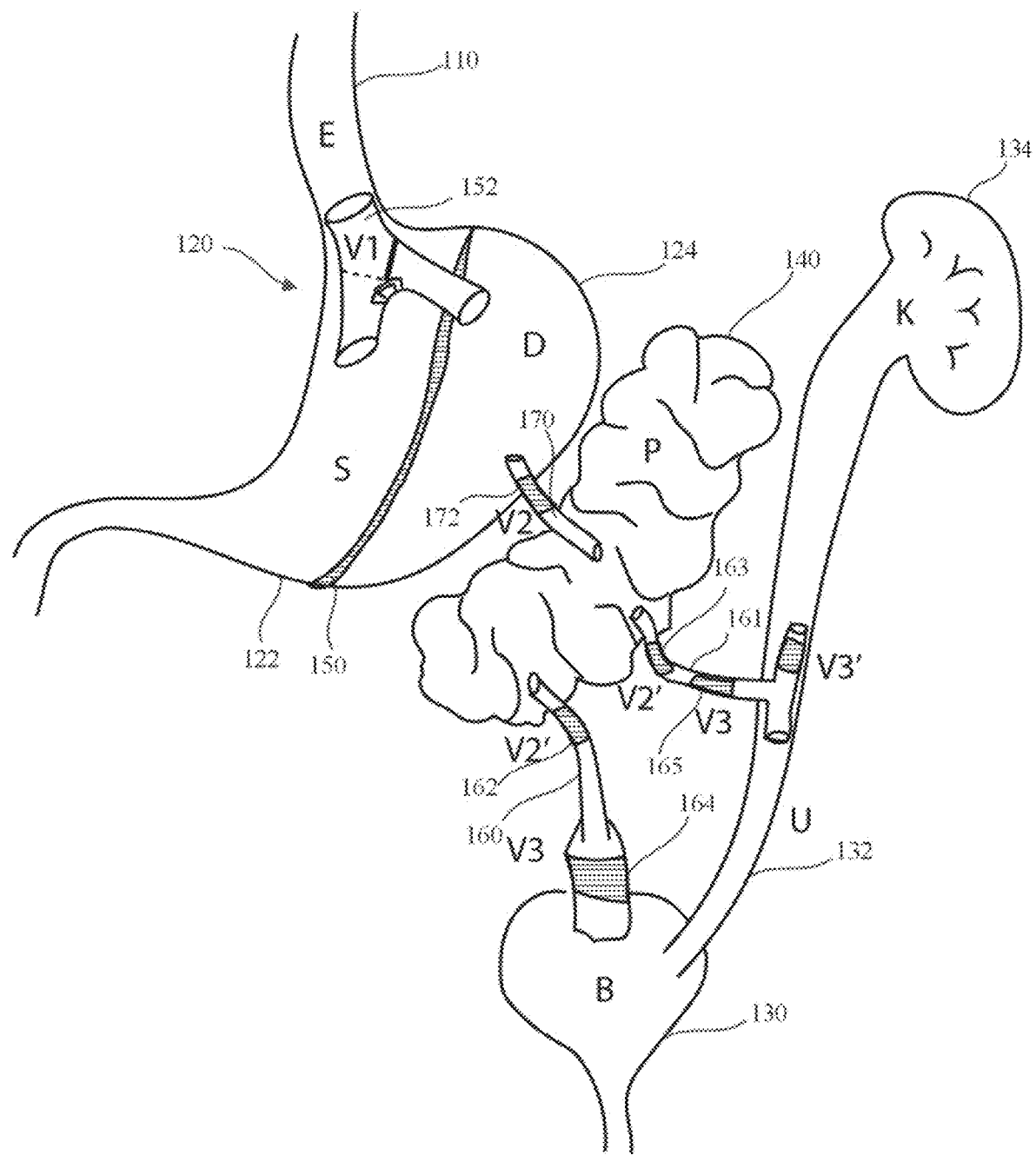
Figure 2:
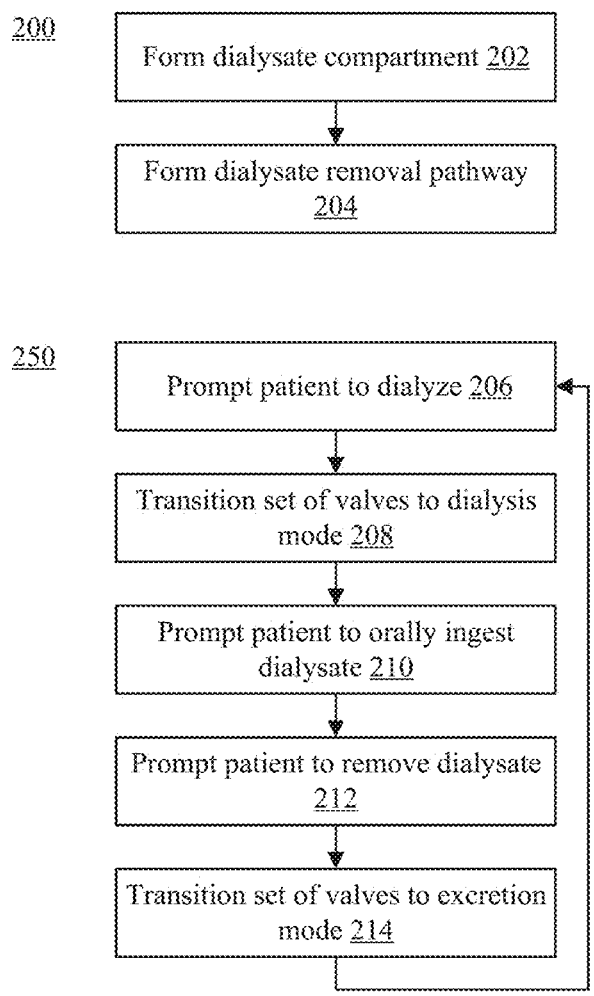
FIG. 2 is an illustrative flowchart of a variation of a method of performing dialysis.

FIGS. 1A-1B illustrate variations of the patient anatomy using the methods described herein. As shown in FIG. 1A, the step of forming a gastric dialysate compartment (202) may comprise performing a non-excising sleeve gastrectomy such that the stomach is divided (150) into two distinct compartments (122, 124). A first flow path may be formed between the esophagus (110) and the stomach compartment (122) using the gastroesophageal valve (152), thereby allowing orally ingestible matter such as food and liquids to begin digestion in the stomach compartment (122) and thereafter in other portions of the gastrointestinal tract. Likewise, a second flow path may be formed between the esophagus and the dialysate compartment (124) through the gastroesophageal valve (152), thereby allowing an orally ingestible dialysate to advance into the dialysate compartment (124) to filter out waste products from the patient. The dialysate compartment (124) may be configured to have a size sufficient to hold a predetermined amount of dialysate. In some variations, the dialysate compartment (124) may undergo one or more of a selective vagotomy, nerve block, or denervation procedure to the nerves innervating the dialysate compartment (124).

FIG. 1A illustrates a first and second urinary tract valve (162, 164) configured to control fluid (e.g., dialysate) flow between the dialysate compartment (124) and the urinary tract (e.g., bladder (130), ureter (132)). A dialysate channel (160) may advance out of the dialysate compartment (124) such that the dialysate may naturally drain out of the dialysate compartment (124) when a first urinary tract valve (162) is in an open position. The first and second urinary tract valves (162, 164) may be placed in a formed first dialysate channel (160). In some variations, the first urinary tract valve (162) may be a unidirectional valve disposed at a first end of the dialysate channel (160) coupled to the dialysate compartment (124), and the second unitary tract valve (164) may be an anti-reflux ball valve disposed at a second end of the dialysate channel (160) coupled to the bladder (130). The second valve (164) may be configured to prevent liquid from advancing into the first dialysate channel (160) and into the dialysate compartment (164). Likewise, a second dialysate channel (161) may be formed at an inferior position of the dialysate compartment (124) such that dialysate may drain into the ureter (132) when a third urinary tract valve (163) is in the open position. The third unitary tract valve (163) may be a unidirectional valve. A fourth unitary tract valve (165) may be disposed between the ureter (132) and second dialysate channel (161). The fourth unitary tract valve (165) may be a T-junction valve configured to prevent backflow into the dialysis compartment (124) and the kidney (134). In other words, fluid flow is directed one-way toward the bladder (130).

FIG. 1B illustrates additional variations of the methods described herein where a peritoneal dialysate compartment (140) may comprise portions of the omentum and/or peritoneum and be surgically formed to create a pouch-like container for dialysate to be held in. In FIG. 1B, a gastric dialysate compartment (124) may be coupled to a peritoneal dialysate compartment (140). For example, a gastroesophageal valve (152) may couple the esophagus (110) to the gastric dialysate compartment (124), and a third dialysate channel (170) may couple the gastric dialysate compartment (124) to the peritoneal dialysate compartment (140). Alternatively, the gastroesophageal valve (152) may directly couple to the peritoneal dialysate compartment (140) through an opening in the stomach (120) (not shown). One or more dialysate valves (172) may be disposed between the gastric dialysate compartment (124) and the peritoneal dialysate compartment (140). For example, the dialysate valve (172) may be a unidirectional valve.

The peritoneal dialysate compartment (140) may be formed and coupled to the urinary tract. For example, a first dialysate channel (160) may be formed at an inferior position of the peritoneal dialysate compartment (140) such that the dialysate may naturally drain out of the peritoneal dialysate compartment (140) and into the bladder (130) when the first urinary tract valve (162) is in the open position. Likewise, a second dialysate channel (161) may be formed at an inferior position of the peritoneal dialysate compartment (140) such that dialysate may drain into the ureter (132) when a third urinary tract valve (163) is in the open position. The third unitary tract valve (163) may be a unidirectional valve. A fourth unitary tract valve (165) may be disposed between the ureter (132) and second dialysate channel (161).

In some variations, the dialysate compartment may comprise the peritoneal cavity such that a gastroesophageal valve may form a direct fluid pathway from the esophagus to the peritoneal cavity. For example, a dialysate output port of the gastroesophageal valve may extend through a stomach wall and into the peritoneal cavity. One or more dialysate channels may be formed to couple the peritoneal cavity to the urinary tract (e.g., bladder, ureter). In some variations, any of the dialysate compartments as described herein may be coupled to a catheter or conduit placed through a patient's abdominal wall for alternative withdrawal of the dialysate.

The conduit may be placed using an open surgical, laparoscopic surgical, or percutaneous procedure. An open surgical procedure may include dissection of an insertion site adjacent to the umbilicus, through dermal and fascia layers to allow access to the peritoneal cavity. The conduit may be inserted into the peritoneal cavity over a stylet. One or more lumens may be formed within the fascia or subcutaneously to retain the conduit. The incision site may be closed with sutures with the external portion of the conduit retained above the skin.

A laparoscopic surgical procedure may involve inserting a trocar at the midline adjacent to the umbilicus, inserted to the depth of the peritoneal cavity with the aid of the pneumoperitoneum. Under scope visualization, the conduit may be inserted over a stylet and placed using graspers and/or other laparoscopic instruments. One or more lumens may be formed within the fascia or subcutaneously to retain the conduit. The incision site may be closed with sutures with the external portion of the conduit retained above the skin.

A percutaneous procedure may be performed adjacent to the umbilicus using the insertion of a small access sheath using a common Seldinger technique. The access sheath may be inserted to the depth of the peritoneal cavity. The conduit may be inserted over a guidewire or a thin stylet and secured in place at an exit site.

In some variations, the implantation process (200) may utilize a guidewire system to aid and confirm formation and patency of an anatomical pathway for dialysate flow through the patient. The guidewire system may be used to locate the anatomical junctions between one or more of the esophagus, stomach, peritoneal cavity, bladder, etc. for the placement of valves and connections between compartments. In some variations, the guidewire system may be used to test the formed surgical path and confirm that orally ingested dialysate flows through the body as intended. Confirmation of the dialysis pathway and valve function may be simulated using the guidewire system before the patient performs oral dialysis. For example, a first guidewire may be inserted through a patient's mouth and esophagus to aid placement of the gastroesophageal valve and/or formation of a dialysate compartment. A second guidewire may be inserted through a patient's urethra to aid placement of one or more urinary tract valves in the bladder, ureter, and dialysate compartment.

In some variations, a guidewire system may be placed along an anatomical path. The anatomical path may comprise a plurality of segments such as between an esophagus and a gastric cavity, the gastric cavity and a peritoneal cavity, the peritoneal cavity and a bladder cavity, and the bladder cavity and a urethra. The guidewire system may include a plurality of guidewires and may include a first guidewire inserted into the esophagus and a second guidewire inserted into the urethra. The guidewires may be placed in one, two, three, or four of the anatomical path segments. In some variations, a single guidewire may be placed along the anatomical segments. In other variations, a guidewire may be inserted through another pathway, such as a conduit created through a patient's abdomen into one or more of a peritoneal cavity and dialysate compartment.

Referring back to the method of FIG. 2, after forming the dialysate flow path (e.g., steps 202, 204), a dialysis process (250) may be performed. A patient may receive a prompt to dialyze at a predetermined time (206). For example, the patient may be prompted using visual, audio, and haptic feedback generated by a computing device such as a smartphone. The patient may receive the prompt from one or more devices using any suitable communication protocol (e.g., audible alert, phone call, text message, pop-up window, vibration, and the like). Once the patient performs an input to acknowledge and/or confirm the prompt, the set of valves may transition to a dialysis mode (208). For example, the gastroesophageal valve may have a default first configuration (e.g., nutrition mode) forming a first path between the esophagus and stomach compartment. The gastroesophageal valve may transition to a second configuration in dialysis mode to form a second path between the esophagus and the dialysate compartment. In some variations, the gastroesophageal valve may perform a self-cleaning operation prior to forming the second path. The self-cleaning operation may comprise transitioning the first valve into a third configuration where ingested matter held within the first valve may be advanced into the stomach compartment. For example, one or more valve components (e.g., discs, filter), as described herein, may be rotated circumferentially to advance any ingested matter into the stomach compartment rather than the dialysate compartment. In the dialysis mode, the set of urinary tract valves may be in a default closed position to prevent fluid flow from the dialysate compartment to the urinary tract.

The patient may receive a prompt to orally ingest the dialysate (210). The patient may perform an input to confirm that they have ingested a predetermined amount of dialysate. Additionally or alternatively, one or more sensors may determine location of dialysate and/or an amount of dialysate removed from a dialysate container to confirm dialysate ingestion. In response, the gastroesophageal valve may transition from the second configuration to the first configuration so as to close the second path between the esophagus and the dialysate compartment, thereby preventing ingested matter such as food ingested after drinking the dialysate from entering the dialysate compartment. Optionally, the self-cleaning operation may be performed prior to transitioning the gastroesophageal valve to the first configuration. In some variations, the gastroesophageal valve may transition from the second configuration to the first configuration after a predetermined amount of time (e.g., a few minutes) in cases where the patient has not ingested the dialysate.

The patient may receive a prompt to excrete the dialysate after a predetermined amount of time from ingesting the dialysate (212). Once the patient performs an input to acknowledge and/or confirm the prompt, the set of valves may transition to an excretion mode (214). For example, the one or more urinary tract valves may transition to an open position configured to permit the dialysate in the dialysate compartment to flow into the urinary tract and be urinated. The one or more urinary tract valves may be opened for a predetermined amount of time corresponding to the time needed for the dialysate to drain into the urinary tract. The gastroesophageal valve may remain in the first configuration in excretion mode. The patient may then urinate as the urge naturally occurs to remove the dialysate and waste products from the body.

In some variations, a communication channel may be established between the computing device and the set of valves to communicate commands and data. In some variations, the set of valves may establish respective communication channels to a plurality of computing devices. The communication channel may be a wired or wireless connection and use any communication including but not limited to those described herein. The communication channel may be established at predetermined intervals based on one or more of time (e.g., hourly), a predetermined schedule stored in valve memory, request for connection, and the like.

Additionally or alternatively, a communication channel may be manually established by a user (e.g., patient, family member, health care professional) at any desired time. The set of valves may establish the communication channel directly or indirectly with one or more computing devices (e.g., smartphone, database, remote server, Internet, and the like) as described herein. For indirect connections, intermediary device(s) may establish additional communication channels. For example, the set of valves may establish a connection to a smartphone to initially transfer valve data and/or sensor data. The smartphone may then transfer the data to a cloud database and/or any other computing device (e.g., remote server). The set of valves may preferably connect to a recognized and/or authorized computing device such as a patient's smartphone and/or desktop PC.

Data stored on a cloud database may be accessible from any account and/or device that is granted access to that data. In some variations, a patient's computing device may connect to another service/platform containing patient data (e.g., valve data, sensor data, dialysis data) to receive that data. Patient data may be analyzed by the computing device, remote server, and the like to optimize the dialysis process. For example, the sequence and/or timing of the dialysis steps (e.g., patient prompts, notifications, valve actuation) may be optimized (e.g., for a pre-determined set of parameters) to improve patient compliance and reduce patient error. In some variations, the sequence and/or timing of dialysis may be adjusted by a physician.

The prompts received by the patient may be output on any accessible computing device. The patient may use a graphical user interface (GUI) to view the patient data, prompts, and/or input commands using one or more of a mobile application (e.g., iOS, Android), web browser accessing a secure website, and/or cloud computing solution. The patient may register an account through the application and login to access its functionality. The displayed prompt may provide information about patient health and dialysis history. The graphical user interface may be displayed in one or more customizable formats. Additionally or alternatively, data, analysis, and/or prompts (e.g., notifications) may include texts and e-mails.

Figure 3:
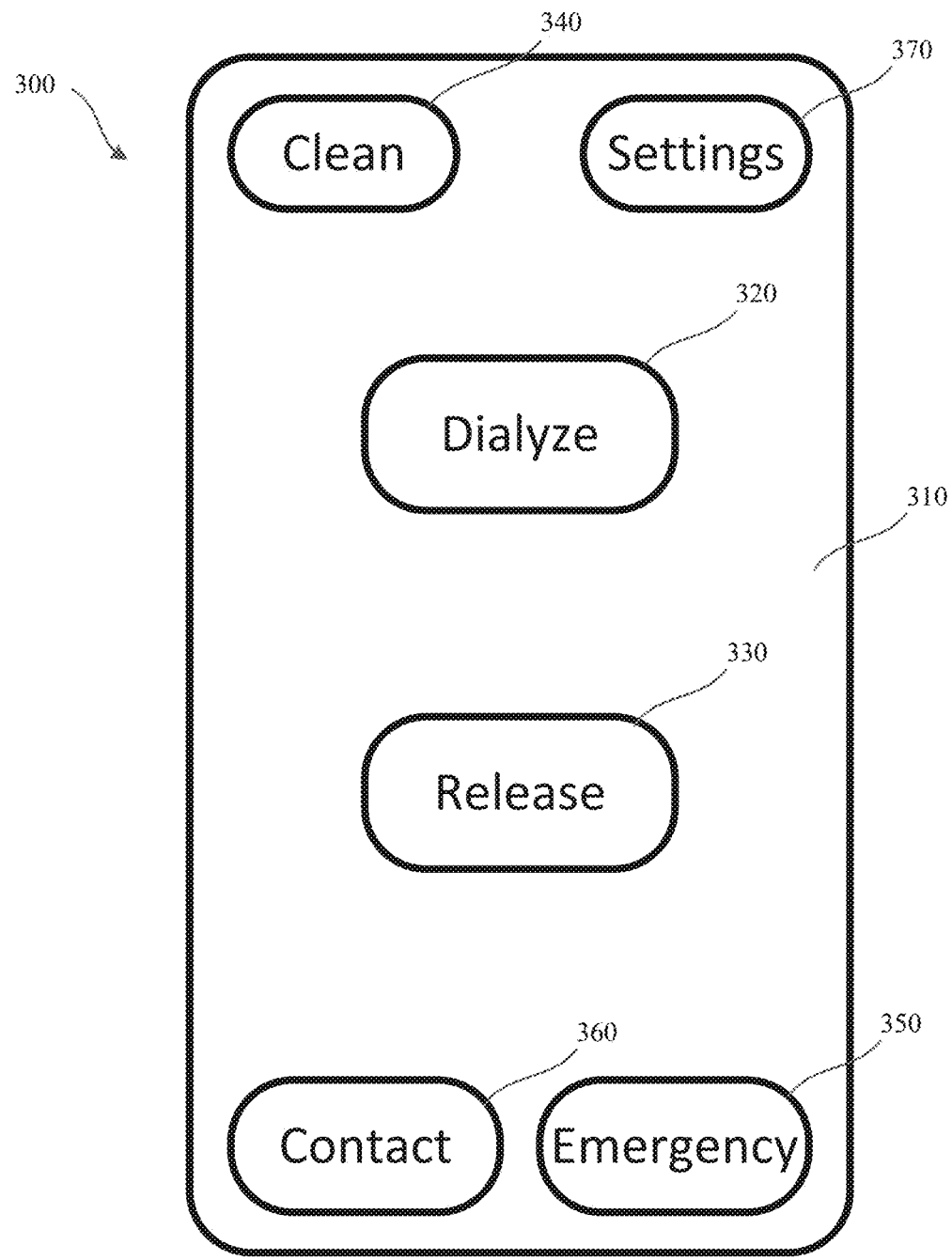
FIG. 3 is an illustrative variation of a graphical user interface.

FIG. 3 is an illustrative variation of a graphical user interface (GUI). The GUI (310) may be output on a computing device (300). The GUI (310) permits a patient to view their dialysis data via any of a mobile application and/or website. The GUI (310) may include a dialyze icon (320) configured to transition the set of valves to a dialysis mode where, for example, a gastroesophageal valve is transitioned to a second configuration, and a release icon (330) for transitioning the set of valves to an excretion mode where, for example, one or more urinary tract valves are transitioned to an open position. In some variations, the dialyze and release icons (320, 330) may be displayed and/or functional at predetermined time periods based on a prescription. One or more of the dialyze and release icons (320, 330) may be accompanied by prompts (e.g., text display in a pop-up window) that may provide additional pertinent information to the patient. For example, the prompt may state, "It is now 10:00 a.m., are you ready to dialyze?" The GUI (310) may include a clean valve icon (340) configured to allow the patient to manually operate the gastroesophageal valve to clear any matter from the valve and to advance it into a stomach compartment for digestion.

One or more contact icons (350, 360) may be displayed to allow the patient to contact one or more predetermined contacts. For example, the emergency contact icon (350) may allow the patient to contact the patient's physician in situations when the patient seeks professional assistance. In some variations, one or more contacts may be designated as an emergency contact that may be automatically notified in the event that the patient's valve data indicate a potentially dangerous situation. For example, a patient computing device may automatically transmit an emergency alert to one or more predetermined contacts in the event that control of one or more of the valves is lost due to, for example, mechanical failure or power loss. The alert may include one or more patient data, valve data, and location of the patient as estimated using the patient's smartphone GPS functionality. In some variations, the patient may designate a set of predetermined contacts (e.g., health care professionals, family, and friends) that may have access to the patient's data. In some variations, the prompts may be output to one or more of the patient and a set of predetermined contacts through mobile Push notifications, text messages, voice calls, and e-mails. For example, a patient's physician may be automatically notified of a patient's non-compliance with a dialysis prescription based on predetermined criteria. If the computing device does not receive an acknowledgment that the physician is taking action within a predetermined period of time, emergency services may be contacted. The contact icon (360) may allow the patient to form a communication channel with a predetermined contact in a non-emergency situation. In some variations, the predetermined contact may receive the patient's communication using the same application that the patient has installed on their own computing device. A settings icon (370) permits the patient to modify device settings including audio and visual settings, haptic feedback, notifications, reminders, predetermined contacts, and the like. Other GUIs (not shown) may be output and allow a patient to view valve data, dialysis history, patient data, and the like.

II. Systems

Figure 4A:
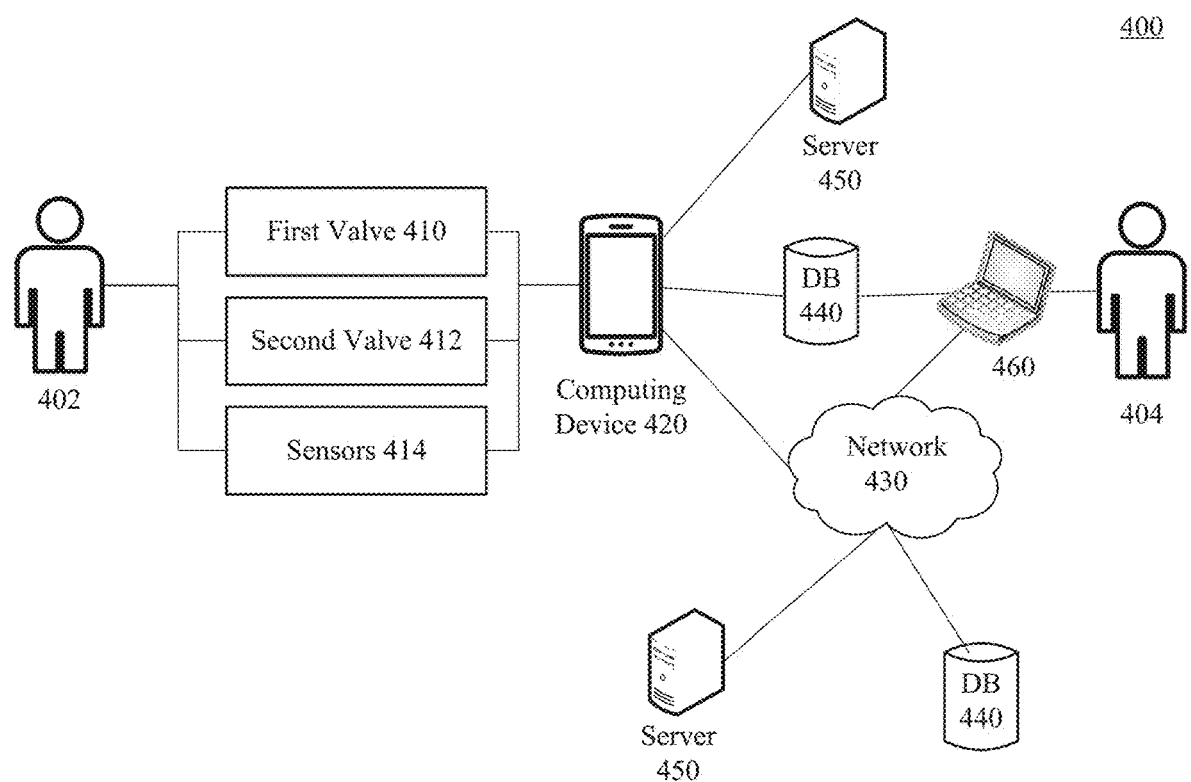
FIGS. 4A-4B are block diagrams of a variation of a disease management system.

A disease management system may include one or more of the components necessary to perform dialysis using the devices as described herein. In addition, the system may be used to ensure patient safety and monitor compliance, usage, and the like. FIG. 4A is a block diagram of a variation of a disease management system (400). The system (400) may comprise a first valve (410) and a second valve (412) each configured to control the flow of ingested matter (e.g., food, dialysate) through the patient (402). In some variations, the system (400) may include one or more sensors (414) configured to track the status of the dialysate and/or patient characteristics. For example, the sensors (414) may be embodied in one or more monitoring device such as a wrist band comprising a proximity sensor that may be worn by the patient and configured to monitor dialysate location and ingestion, and one or more dialysate container sensors configured to measure dialysate ingestion through flow and volume. As additional examples, the sensor (414) may be embodied in the first valve (410) and comprise one or more of a pH sensor and flow meter and configured to monitor dialysate flow through the valve (410). The first valve (410), second valve (412), and sensors (414) may be coupled to a computing device (420) through one or more wired or wireless communication channels. The computing device (420) may be coupled one or more networks (430), databases (440), and/or servers (450). The network (430) may comprise one or more databases (440) and servers (450). In some variations, a health care professional (HCP) (404) may be coupled one or more networks (430), databases (440), and servers (450) through a respective computing device (460). In some variations, one or more of the first valve (410), second valve (412), and sensors (414) may be coupled directly to any of the network (430), database (440), server (450), or each other. Processing and analysis may be performed at any one of the devices of the system (400) or distributed throughout a plurality of devices.

Gastroesophageal Valve

A gastroesophageal valve (500) may be configured to selectively switch between different flow paths to direct the flow of non-dialysate matter and dialysate fluid into appropriate body cavities (e.g., stomach compartment for food, dialysate compartment for dialysate). The valve (500) may comprise a housing configured with a size and shape suited for placement in a patient's gastroesophageal junction. For example, the valve (500) may comprise branches having a diameter of about 20 mm. The valve (500) may comprise one or more safety mechanisms and sensors to ensure ingested matter is directed to the desired body cavity. For example, the valve (500) may comprise a filter configured to allow passage of dialysate and prevent particulate matter (e.g., food) above a predetermined size from entering a dialysate compartment (e.g., gastric sleeve, peritoneal cavity). The filter may comprise one or more of a microporous mesh, web, perforations, multi-layer and/or multi-filament cross-fiber configuration. In some variations, the filter may be formed of one or more biocompatible materials including polymers such as cellulose-based compounds, PTFE, nylon, polysulfone, polycarbonate, and the like. In some variations, the valve (500) may comprise a UV light source (e.g., UV-C LED light source) configured to emit UV light within the first valve to disinfect ingested dialysate and/or non-dialysate ingested matter. For example, the UV light source may be disposed in a dialysate flow path in the valve. The valve configurations as described herein are merely illustrative. The devices, systems, and methods described here may comprise one or more of the devices described in U.S. Pat. No. 6,979,351, filed Aug. 1, 2003, and titled "IMPLANTABLE CERAMIC VALVE PUMP ASSEMBLY," the contents of which are hereby incorporated by reference in their entirety.

Figure 5A:
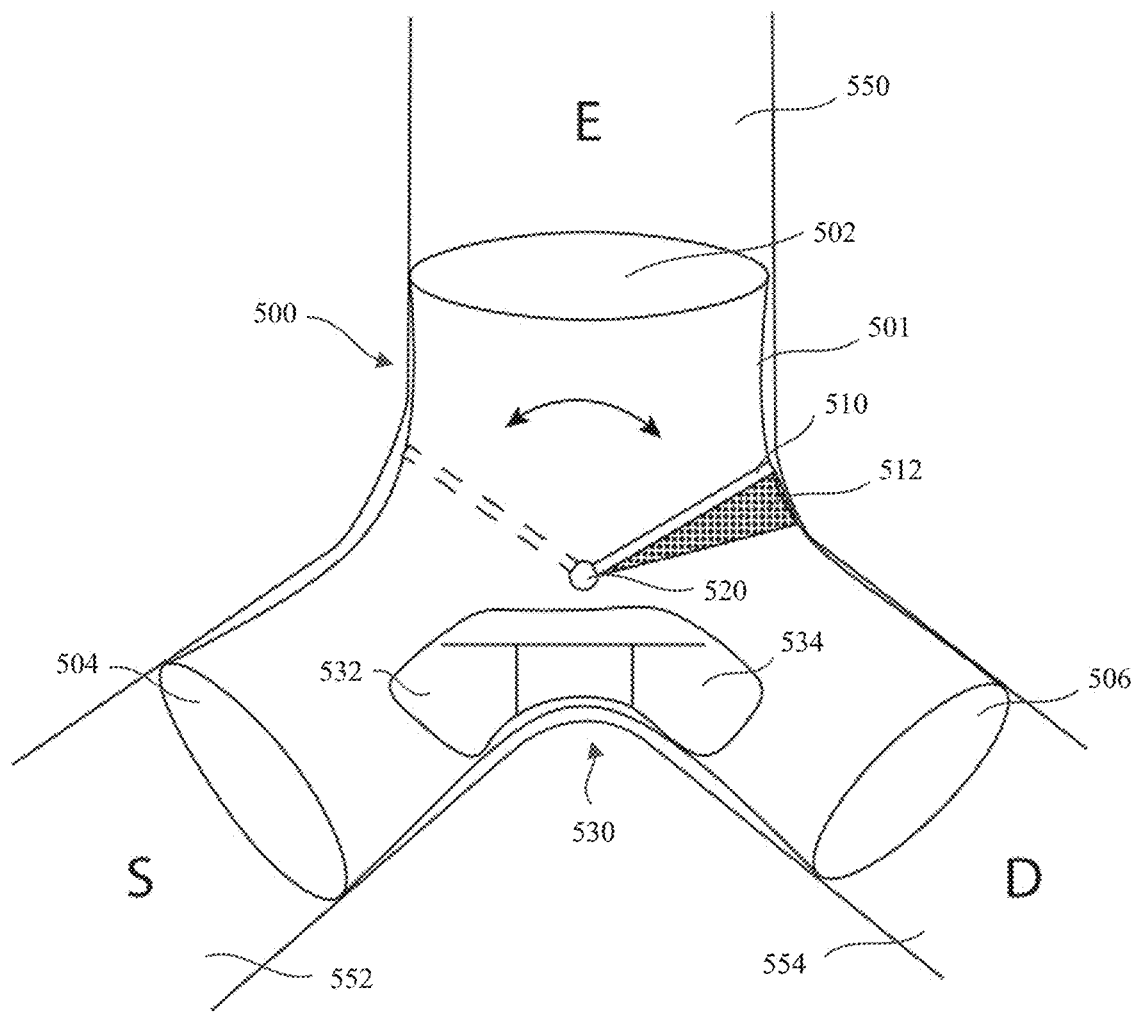
FIGS. 5A-5C are illustrative cross-sectional schematic views of an exemplary variation of a gastroesophageal valve.
Figure 5B:
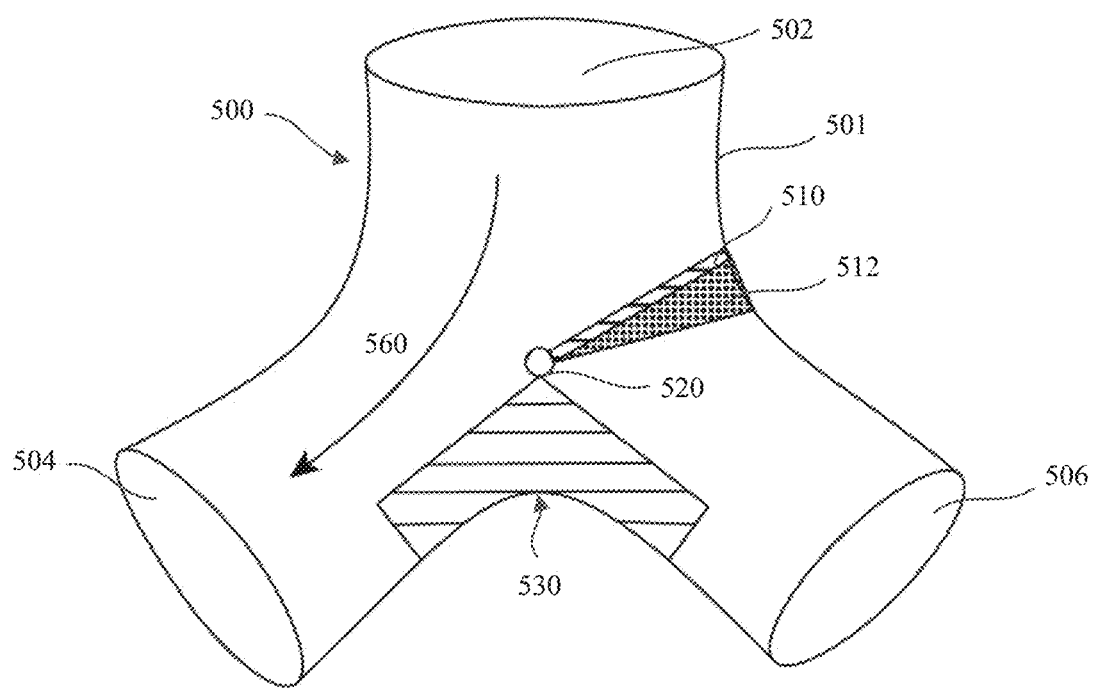
Figure 5C:
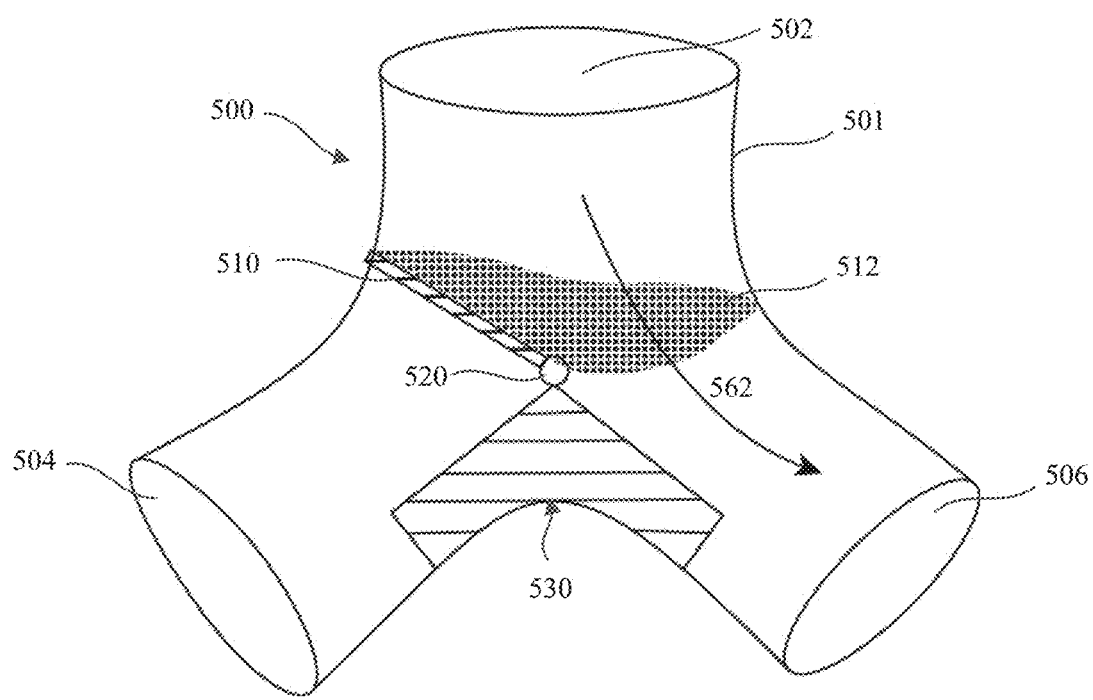

FIGS. 5A-5C are illustrative views of a gastroesophageal valve (500) disposed in a gastroesophageal junction of a patient. The valve (500) as depicted in the cross-sectional schematic view of FIGS. 5A-5C may comprise an input port (502) coupled to an esophagus (550), a first output port (504) coupled to a stomach compartment (552), and a second output port (506) coupled to a dialysate compartment (554). A disc (510) may be coupled to a rotatable axis (520) coupled to an actuator (not shown) such that the disc (510) rotates about the axis (520). The disc (510) may comprise any shape, materials, structure, etc. able to form a selectable physical barrier to ingested matter within the valve (500) to divert the ingested matter into a desired compartment. For example, the disc (510) may comprise a fin-like projection, membrane, and/or blade. The disc (510) may be rotated between a first and second configuration by the actuator (520) to form respective paths between the esophagus (550) and either the stomach or dialysate compartments. The valve (500) may further comprise a controller (530) to control the valve (500). The controller (530) may comprise a transceiver (532) configured to communicate with a computing device and a power source (534) to power the controller (530) and actuator. For example, the controller (530) may comprise one or more components of a computing device (e.g., processor, memory, transceiver) as described herein.

FIG. 5B illustrates the valve (500) in a first configuration where the valve (500) forms a first path (560) between the input port (502) and first output port (504) (e.g., between the esophagus and stomach compartment). Accordingly, ingested matter such as non-dialysate food may advance from the esophagus (550) and into the stomach compartment (552) and gastrointestinal tract for digestion. In the first configuration, the disc (510) forms a physical barrier to block ingested matter from passing through the second output port (506) and into a dialysate compartment (554). The disc (510) in the first configuration may be disposed such that matter in contact with its surface will naturally slide or advance out of the first output port (504) and into the stomach compartment (552). For example, the disc (510) in the first configuration may be angled relative to ground. Any matter that remains may be advanced out of the first output port (504) through rotation of the disc (510) towards first output port (504) such as shown in FIG. 5C. The disc (510) may be coupled to a flexible filter (512) or the filter (512) may be separated from the disc (510). FIG. 5B depicts a flexible filter (512) in a folded configuration. The controller (530) is depicted as disposed within a lumen of the valve (500) but may be disposed on an external surface of the valve (500).

FIG. 5C illustrates the valve (500) in a second configuration where the valve (500) forms a second path (562) between the input port (502) and the second output port (506) (e.g., between the esophagus and dialysate compartment). Accordingly, ingested matter such as dialysate may advance from the esophagus (550) and into a dialysate compartment (554) (e.g., peritoneal cavity). In the second configuration, the disc (510) forms a physical barrier to block ingested matter from passing through the first output port (504) and into a stomach compartment (552). The disc (510) in the second configuration may be disposed such that dialysate in contact with its surface will flow out of the second output port (506) and into the dialysate compartment. The filter may comprise a plurality of holes (e.g., mesh) configured to permit dialysate to flow through and prevent non-dialysate matter such as food particles from passing through the filter (512). The filter (512) may be coupled between the disc (510) and an inner wall of the valve (500) and configured to capture any matter over a predetermined particle size from passing through the second path (562) and into the dialysate compartment. In some variations, the filter (512) may be coupled between the axis (520) and the inner wall of the housing (501). The filter (512) may be flexible or stiff. FIG. 5C depicts a flexible filter (512) in an unfolded configuration. In some variations, the disc (510) may be further rotated toward ground towards the first output port (504) such that matter held by the filter (512) may fall into the stomach compartment through gravity using the first path (560).

As shown in FIGS. 5A-5C, the valve (500) may comprise a housing (501) configured to receive ingested matter from the esophagus and direct the matter into an appropriate body cavity through one of two flow paths (560, 562). The input and output ports (502, 504, 506) of the housing (501) may have any suitable diameter and length. The housing (501) may be formed of any biocompatible material including, but not limited to epoxy, Teflon, PVS, ABS plastic, silicone, polyvinyl chloride, latex, polyurethane, polyethylene, PTFE, and nylon.

The disc (510) may comprise any shape, configuration, and/or material suitable to block matter falling through the esophagus from entering a blocked flow path. In some variations, the disc may comprise flat plane shape, such as a blade or knife shape. In some variations, the disc (510) may comprise non-flat shapes and/or a plurality of portions, such as portions having different angular faces, curves, elevations, thicknesses, and the like. As shown in FIGS. 5A-5C, the disc (510) is rotated about the axis (520). The disc (510) may be actuated by one or more actuators. In some variations, the valve (500) may comprise respective discs for each flow path, with each disc slidable along a longitudinal axis of the disc to open and close the flow path.

In some variations, the valve (500) receives control signals wirelessly from an external computing device (e.g., smartphone). In the absence of externally-received control signals, the controller (530) may store instructions in memory to operate the valve (500). For example, if the valve (500) has been left in the second configuration for a predetermined amount of time (e.g., five minutes or more), the patient has likely forgotten to switch the valve (500) back from the dialysis mode to a nutrition mode. In some variations, the controller (530) may override a set of received control signals using a set of predetermined criteria. The power source (534) of the controller (530) may be used to operate components of the valve including the actuator and may comprise an internal battery, wireless power system, and the like. For example, the power source may comprise an inductive charging system.

Figure 6A:
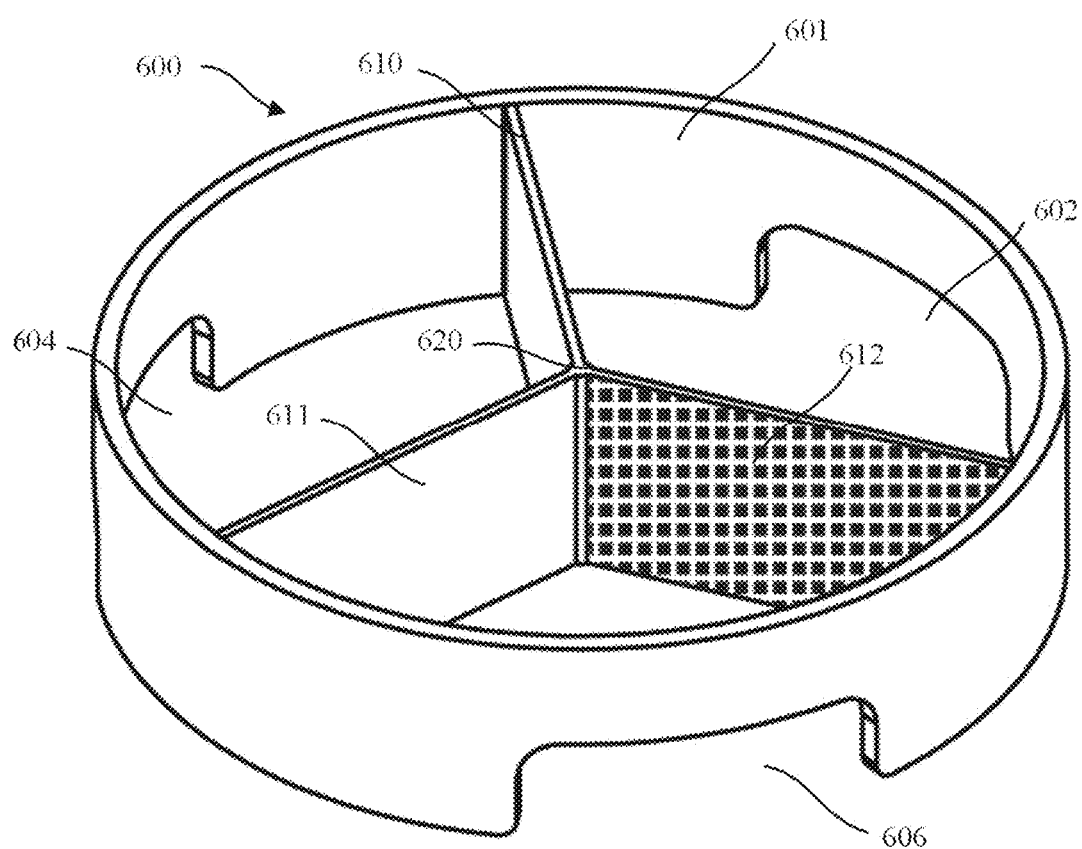
FIGS. 6A-6D are illustrative views of another exemplary variation of a gastroesophageal valve.

FIGS. 6A-6D are directed to another variation of a gastroesophageal valve (600). FIG. 6A is a cut-away perspective view of a valve (600) comprising a housing (601) including an input port (602), first output port (604), and second output port (606). A first disc (610), second disc (611), and filter (612) may be coupled to and rotate about an axis (620) coupled to an actuator (not shown). Each of the first disc (610), second disc (611), and filter (612) may rotate independently about the axis (620).

Figure 6B:
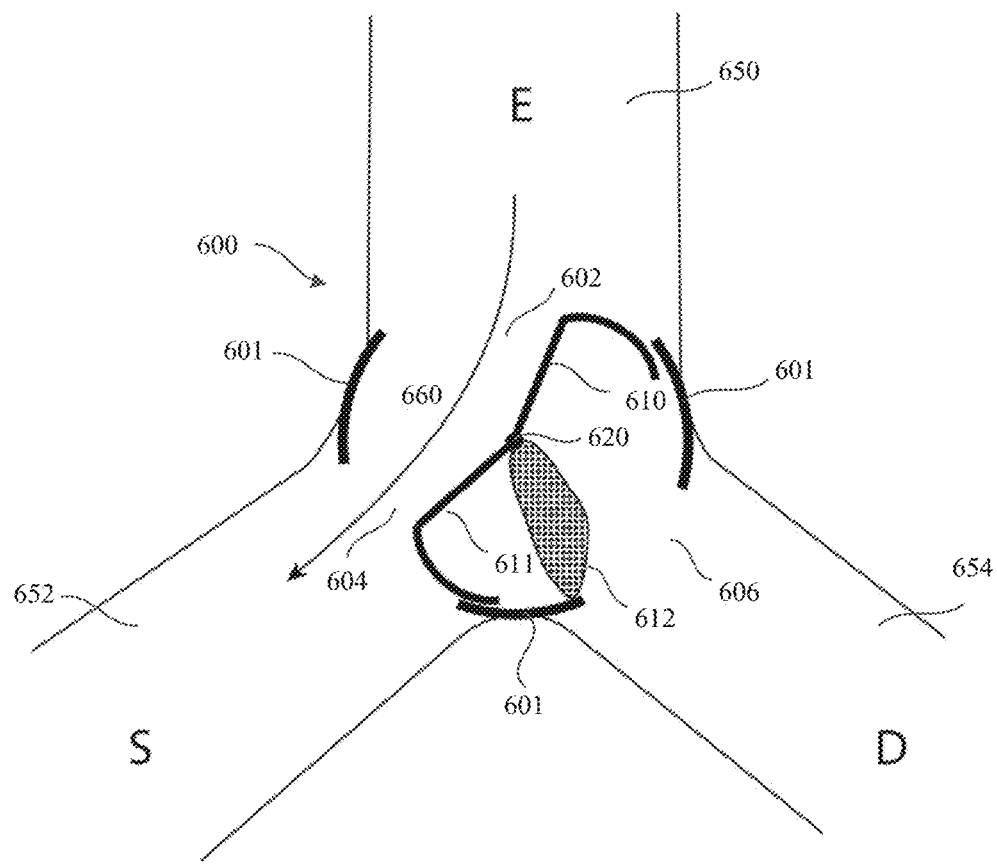
Figure 6C:
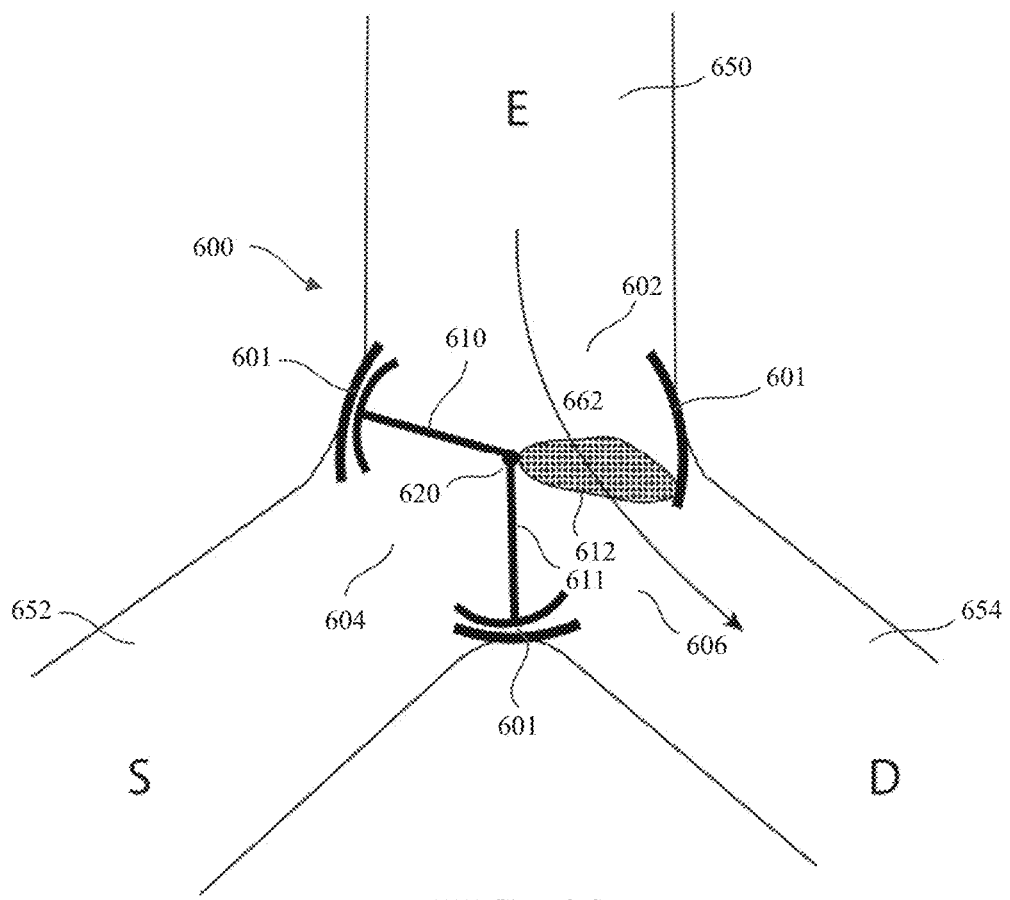
Figure 6D:
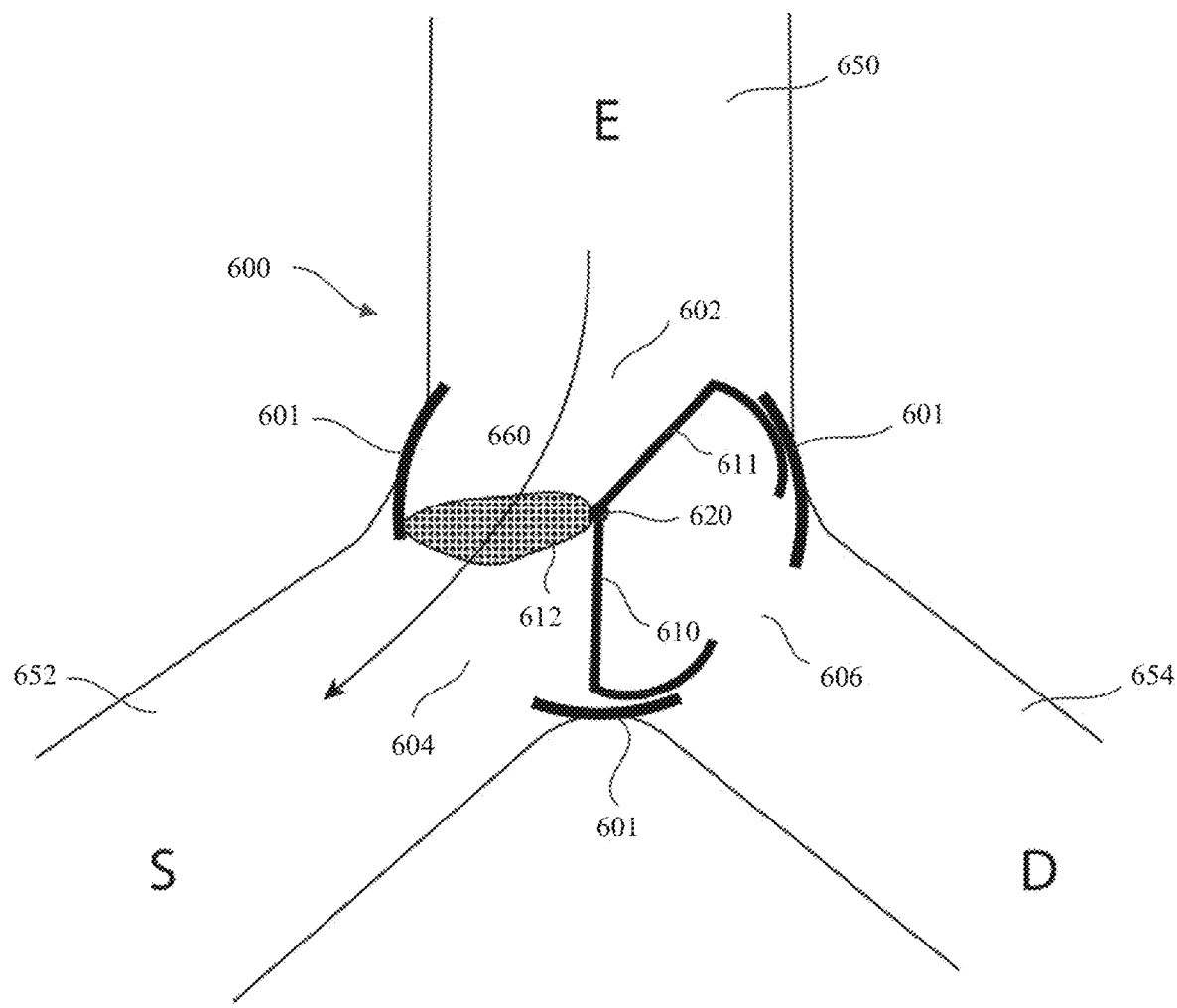

FIGS. 6B-6D are cross-sectional schematic views of the valve (600) disposed in a gastroesophageal junction of a patient. The first disc (610), second disc (611), and filter (612) may be rotated about the axis (620) between a first configuration (FIG. 6B), second configuration (FIG. 6C), and third configuration (FIG. 6D). Rotation of the discs (610, 611) and filter (612) between the first configuration and second configuration by one or more actuators may form respective paths between the esophagus and either the stomach or dialysate compartments. The third configuration may allow non-dialysate matter held on a surface of the filter (612) to be rotated into the first path (660) such that the non-dialysate matter falls away from the filter (612) and into the stomach compartment (652) through gravity. In the third configuration, liquid and/or matter smaller than the holes in the filter (612) may flow through the filter (612) and through the first path (660). The valve (600) may further comprise a controller (not shown for clarity) to control the valve (600). The controller may comprise a transceiver configured to communicate with a computing device and a power source to power the controller and actuator. For example, the controller may comprise one or more components of a computing device (e.g., processor, memory, transceiver) as described herein.

FIG. 6B illustrates the valve (600) in a first configuration where the valve (600) forms a first path (660) between the input port (602) and first output port (604) (e.g., between the esophagus and stomach compartment). Accordingly, ingested matter such as non-dialysate food may flow from the esophagus (650) and into the stomach compartment (654) and gastrointestinal tract for digestion. The input port (602) may be coupled to an esophagus (650), the first output port (604) may be coupled to a stomach compartment (652), and a second output port (606) may be coupled to a dialysate compartment (654). In the first configuration, the first and second discs (610, 611) are positioned to form a physical barrier to block ingested matter from passing through the second output port (606) and into the dialysate compartment (654). The first and second discs (610, 611) in the first configuration may be disposed such that matter in contact with their surfaces will naturally slide or advance out of the first output port (604) and into the stomach compartment (652). In other words, the first and second discs (610, 611) in the first configuration may be angled relative to ground. Any matter that remains on the first and second discs (610, 611) may be advanced out of the first output port (604) through rotation of the discs (610, 611) towards ground such as shown in FIG. 6C. The discs (610, 611) may be independently rotatable.

FIG. 6C illustrates the valve (600) in a second configuration where the valve (600) forms a second path (654) between the input port (602) and the second output port (606) (e.g., between the esophagus and dialysate compartment). In this manner, ingested matter such as dialysate may flow from the esophagus and into a dialysate compartment (e.g., peritoneal cavity, gastric sleeve). In the second configuration, the first disc (610) forms a physical barrier configured to block ingested matter from passing through the first output port (604) and into the stomach compartment (652). The first disc (610) in the second configuration may be disposed such that dialysate in contact with its surface will flow through the filter (612) and out of the second output port (606) and into the dialysate compartment (654). As described herein, the filter (612) may comprise a plurality of holes configured to permit dialysate to flow through and prevent non-dialysate matter such as food particles from passing through the filter (612). The filter (612) may be configured to capture any non-dialysate matter over a predetermined particle size from passing through the second path (662) and into the dialysate compartment (654).

In some variations, as shown in FIG. 6D, the first and second discs (610, 611) and filter (612) may be rotated about axis (620) to a third configuration such that any matter disposed on the filter (612) will fall away from the filter (612) and into the stomach compartment (652) through gravity. The valve (600) may transition to the third configuration after the second configuration to ensure that any digestible matter disposed on the filter (612) is advanced into the stomach compartment (652) rather than remaining on the filter (612). In some variations, after ingesting a dialysate with the valve (600) in the second configuration, the valve (600) may transition to the third configuration and a patient may be prompted to ingest a liquid (e.g., water) to clear (e.g., clean) any matter from the filter (612) and ensure that any non-dialysate matter on the filter (612) is advanced into the stomach compartment (652). The first disc (610), second disc (611), and filter (612) may each be independently rotatable.

As shown in FIGS. 6A-6D, the valve (600) may comprise a housing (601) configured to receive ingested matter from the esophagus and be configured to direct the matter into an appropriate body cavity through one of two flow paths (660, 662). The input and output ports (602, 604, 606) of the housing (601) may have any suitable diameter and length. The housing (601) may be formed of any biocompatible material including, but not limited to epoxy, Teflon, PVS, ABS plastic, silicone, polyvinyl chloride, latex, polyurethane, polyethylene, PTFE, and nylon.

The first and second discs (610, 611) may comprise any shape, configuration, and/or material suitable to block matter falling through the esophagus from entering a blocked flow path. In some variations, the discs may comprise flat plane shape, such as a blade or knife shape. In some variations, the discs (610, 611) may comprise non-flat shapes and/or a plurality of portions, such as portions having different angular faces, curves, elevations, thicknesses, and the like. As shown in FIGS. 6B-6D, the discs (610, 611) may be rotated about the axis (620). The discs (610, 611) may be actuated by one or more actuators.

In some variations, the valve (600) may receive control signals wirelessly from an external computing device (e.g., smartphone). In the absence of externally-received control signals, a controller may store instructions in memory to operate the valve (600). For example, if the valve (600) has been left in the second configuration for a predetermined amount of time (e.g., ten minutes or more), the patient has likely forgotten to switch the valve (600) back from the dialysis mode to nutrition mode. In some variations, the controller may override a set of received control signals using a set of predetermined criteria. A power source of the controller may be used to operate components of the valve including the actuator and may comprise an internal battery, wireless power system (e.g., inductive charging, magneto-dynamic coupling), and the like. For example, the valve power source may comprise a near field (e.g., non-radiative) inductive power receiver such as a secondary induction coil for receiving energy transferred from an electromagnetic field generated by a primary induction coil of an external charging device. The secondary induction coil may convert the received energy into electric current to power one or more valve components such as the actuator and controller. In some variations, the dialysate bottle may comprise the external charging device where close proximity of the valve to the dialysate bottle may power the valve during a dialysis process.

Computing Device

Figure 4B:
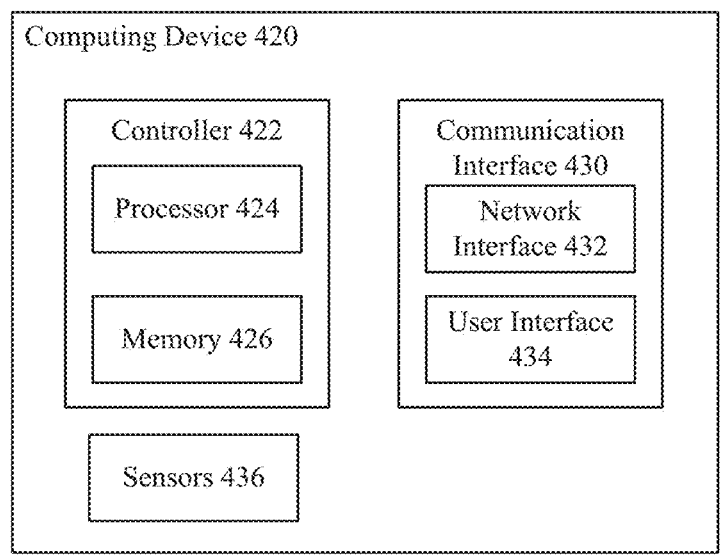

The valves as described herein may couple to one or more computer systems and/or networks. FIG. 4B is a block diagram of the computing device (420). The computing device (420) may comprise a controller (422) comprising a processor (424) and a memory (426). In some variations, the computing device (420) may further comprise one or more of a communication interface (430). The controller (422) may be coupled to the communication interface (430) to permit an operator (e.g., patient) to control the computing device (420), valves (4210, 412), sensors (414), and any other component of the system (400). The communication interface (430) may comprise a network interface (432) configured to connect the computing device (420) to another system (e.g., Internet, remote server, database) over a wired and/or wireless network. The communication interface (430) may further comprise a user interface (434) configured to permit a patient to directly control the computing device (420). The computing device (420) may further comprise one or more sensors (436) that may be configured to monitor the proximity of the dialysate to the computing device. The sensors (436) may be coupled to the controller (422) configured to receive and process the sensor data from the sensors (436).

A. Controller

A computing device (420), as depicted in FIG. 4B, may comprise a controller (422) in communication with one or more valves (410, 412), and sensors (414). The controller (520) may comprise one or more processors (424) and one or more machine-readable memories (426) in communication with the one or more processors (424). The processor (424) may incorporate data received from memory (426) and patient input to control the system (400) (e.g., one or more valves (410, 412). The memory (426) may further store instructions to cause the processor (424) to execute modules, processes and/or functions associated with the system (400). The controller (422) may be connected to the one or more valves (410, 412) by wireless communication channels. The controller (220) may be configured to control one or more components of the system (400), such as valves (410, 412), communication interface (430), and the like.

The controller (422) may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks. Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an patient's environment through sensors and may use head-mounted displays for visualization, eye gaze tracking, and user input.

i. Processor

The processor (424) may be any suitable processing device configured to run and/or execute a set of instructions or code and may include one or more data processors, image processors, graphics processing units, physics processing units, digital signal processors, and/or central processing units. The processor (424) may be, for example, a general purpose processor, Field Programmable Gate Array (FPGA), an Application Specific Integrated Circuit (ASIC), and/or the like. The processor (424) may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

ii. Memory

In some variations, the memory (426) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory (426) may store instructions to cause the processor (424) to execute modules, processes and/or functions associated with the computing device (400), such as valve control, signal data processing, sensor control, communication, and/or user settings. In some variations, storage may be network-based and accessible for one or more authorized users. Network-based storage may be referred to as remote data storage or cloud data storage. EMG signal data stored in cloud data storage (e.g., database) may be accessible to respective users via a network, such as the Internet. In some variations, database (440) may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

B. Communication Interface

The communication interface (430) may permit a patient to interact with and/or control the system (400) directly and/or remotely. For example, a user interface (434) of the system (400) may include an input device for a patient to input commands and an output device for a patient and/or other observers to receive output (e.g., view patient data on a display device) related to operation of the system (400). In some variations, a network interface (432) may permit the computing device (400) to communicate with one or more of a network (430) (e.g., Internet), remote server (450), and database (440) as described in more detail herein.

i. User Interface

User interface (434) may serve as a communication interface between a patient and the computing device (420). In some variations, the user interface (434) may comprise an input device and output device (e.g., touch screen and display) and be configured to receive input data and output data from one or more of the sensors (414, 436), input device, output device, network (430), database (440), and server (450). For example, flow rate data generated by a flow sensor (414) may be processed by processor (424) and memory (426), and displayed by the output device (e.g., smartphone display). Sensor data from one or more sensors (414, 436) may be received by user interface (434) and output visually, audibly, and/or through haptic feedback through one or more output devices. As another example, patient control of an input device (e.g., joystick, keyboard, touch screen) may be received by user interface (434) and then processed by processor (424) and memory (426) for user interface (434) to output a control signal to one or more valves (410, 412).

1. Output Device

An output device of a user interface (434) may output sensor data corresponding to a patient and/or system (400), and may comprise one or more of a display device, audio device, and haptic device. The display device may be configured to display a graphical user interface (GUI). A display device may permit a patient to view patient data (e.g., valve data, dialysate data) and/or other data processed by the controller (422). In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

An audio device may audibly output patient data, valve data, sensor data, system data, alarms and/or warnings. For example, the audio device may output an audible warning when a patient has not ingested a predetermined quantity of dialysate within a predetermined period of time or when a malfunction in the valves (410, 412) is detected. In some variations, an audio device may comprise at least one of a speaker, piezoelectric audio device, magnetostrictive speaker, and/or digital speaker. In some variations, a patient may communicate with other users using the audio device and a communication channel. For example, the patient may form an audio communication channel (e.g., VoIP call) with a health care professional and/or family member.

A haptic device may be incorporated into one or more of the input and output devices to provide additional sensory output (e.g., force feedback) to the patient. For example, a haptic device may generate a tactile response (e.g., vibration) to confirm patient input to an input device (e.g., touch surface). Haptic feedback may in some variations confirm a transition of a valve between different positions within the patient (e.g., closed to open urinary tract valve). Additionally or alternatively, haptic feedback may notify that patient input is overridden by the system to prevent potential harm to the patient and/or system.

2. Input Device

Some variations of an input device may comprise at least one switch configured to generate a control signal. In some variations, the input device may comprise a wired and/or wireless transmitter configured to transmit a control signal to a wired and/or wireless receiver of a controller (422). For example, an input device may comprise a touch surface for a patient to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive patient movement data from an optical sensor and classify a patient gesture as a control signal. A microphone may receive audio and recognize a patient voice as a control signal.

ii. Network Interface

As depicted in FIG. 4B, a computing device (420) described herein may communicate with one or more networks (430) and computer systems (450) through a network interface (432). In some variations, the computing device (420) may be in communication with other devices via one or more wired and/or wireless networks. The network interface (432) may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface (432) may comprise a radiofrequency receiver, transmitter, and/or optical (e.g., infrared) receiver and transmitter configured to communicate with one or more devices and/or networks. The network interface (432) may communicate by wires and/or wirelessly with one or more of the sensors (414), user interface (434), network (430), database (440), and server (450).

In some variations, the network interface (430) may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, near-field communication (NFC), radio-frequency identification (RFID), Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet Message Access Protocol (IMAP) and/or Post Office Protocol (POP)), instant messaging (e.g., eXtensible Messaging and Presence Protocol (XMPP), Session Initiation Protocol for Instant Messaging and Presence Leveraging Extensions (SIMPLE), and/or Instant Messaging and Presence Service (IMPS)), and/or Short Message Service (SMS), or any other suitable communication protocol. Some wireless network deployments combine networks from multiple cellular networks or use a mix of cellular, Wi-Fi, and satellite communication. In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

Monitoring Device

A monitoring device as used herein may refer to any device configured to measure and/or analyze one or more characteristics of a patient and/or dialysate. A monitoring device may, for example, monitor a dialysate and generate patient data. Non-limiting examples of monitoring devices include diagnostic devices. Patient and dialysate data generated by the monitoring device may include, but is not limited to, dialysate location, dialysate flow, dialysate volume, pH measurements, patient location, and the like. The data generated by the monitoring device may be transmitted to any of the devices of the system (400), and may include one or more of the features, elements, and/or functionality of the computing devices, as described herein. For example, the monitoring device may comprise a controller comprising a processor and memory to perform data analysis on the patient and dialysate data generated by the monitoring device and a communication interface configured to transmit the data to another device. The monitoring device may couple to a device using any known wired or wireless connection method and communication protocol, such as Bluetooth, RFID, NFC, and the like.

In some variations, the monitoring device may comprise one or more proximity sensors disposed on one or more of a dialysate container (e.g., disposed within a portion of a dialysate bottle), wrist-based proximity sensor, and patient computing device. The proximity of the dialysate container to one or more of a patient's wrist sensor and computing device may be used to control the gastroesophageal valve (e.g., transition the first valve to a second configuration). For example, the first valve may transition to a dialysis mode only upon patient input to a GUI of the computing device and upon detection of a dialysate container within a predetermined distance of a patient's wrist-based proximity sensor. This may ensure that valve switching does not occur if the patient is not near enough to the dialysate container to consume the prescribed dialysate. This may help prevent a patient from damaging themselves by accidentally activating a dialysis mode on their computing device and drinking a non-dialysate liquid.

In some variations, the monitoring device may comprise one or more volume and/or flow sensors configured to determine an amount of dialysate ingested by a patient. The volume and/or flow sensors may be disposed in one or more of a dialysate container and a gastroesophageal valve. Upon detection that a predetermined volume of dialysate has been ingested, the gastroesophageal valve may transition from the dialysis mode to the nutrition mode (e.g., transition from the second configuration to the first configuration). If a patient has not consumed a predetermined volume of dialysate within a predetermined amount of time, the computing device may output a warning and/or notification to one or more of the patient and predetermined contacts. In some variations, the gastroesophageal valve may remain in the dialysis mode until the predetermined volume of dialysate has been ingested. Data generated by the one or more monitoring devices may be transmitted to a remote server and/or database and be used to analyze patient compliance.

The specific examples and descriptions herein are exemplary in nature and variations may be developed by those skilled in the art based on the material taught herein without departing from the scope of the present invention, which is limited only by the attached claims.

The invention claimed is:

1. A device, comprising:
   a transceiver configured to communicate with a gastroesophageal junction valve;
   an input device configured to receive a control signal to control flow of ingested matter through the gastroesophageal junction valve;
   an output device configured to output data to the patient; and
   a controller coupled to the transceiver, the input device, and the output device, the controller comprising a processor and a memory, and the controller configured to control the gastroesophageal junction valve based on the received control signal to permit fluid in the ingested matter to flow into a fluid compartment and the ingested matter not comprising the fluid to advance into a stomach compartment.

2. The device of claim 1, wherein the transceiver is configured to communicate with a urinary tract valve disposed in a patient, the input device is configured to receive the control signal from the urinary tract valve, and the controller is configured to open the urinary tract valve such that the fluid in the fluid compartment is permitted to flow into a urinary tract for urination.

3. The device of claim 2, wherein the controller is configured to output a first prompt to ingest the fluid using a predetermined schedule using a computing device comprising a processor and memory, and output a second prompt to transition the second valve to the open position using a predetermined schedule.

4. The device of claim 3, wherein the controller is configured to notify a set of predetermined contacts of a status of the gastroesophageal junction valve and the urinary tract valve.

5. The device of claim 2, wherein the controller is configured to transmit an emergency alert in response to loss of control of the urinary tract valve, the emergency alert comprising one or more of patient data, valve data, and location data of the patient.

6. The device of claim 2, wherein the urinary tract valve is formed at an inferior position relative to the fluid compartment.

7. The device of claim 2, wherein the urinary tract valve comprises at least one urinary tract valve, wherein the at least one urinary tract valve comprises one or more of a bladder valve and a urethra valve.

8. The device of claim 2, wherein the urinary tract valve comprises at least one urinary tract valve, wherein the at least one urinary tract valve comprises one or more of a unidirectional valve and an anti-reflux ball valve.

9. The device of claim 1, wherein the controller is configured to advance the ingested matter held within the gastroesophageal junction valve into the stomach compartment.

10. The device of claim 1, wherein the controller is configured to control the gastroesophageal valve using proximity data of the patient and the fluid generated by a proximity sensing device.

11. The device of claim 1, wherein the fluid compartment comprises a peritoneal cavity.

12. The device of claim 1, wherein the urinary tract valve is coupled to a fluid channel formed between the fluid compartment and a urinary tract of the patient.

13. The device of claim 1, wherein the gastroesophageal junction valve comprises a filter configured to allow passage of the fluid dialysate and prevent the ingested matter not comprising the fluid from entering the fluid compartment.

* * * * *